United States Patent [19]
Becker et al.

[11] Patent Number: 5,814,094
[45] Date of Patent: Sep. 29, 1998

[54] IONTOPHERETIC SYSTEM FOR STIMULATION OF TISSUE HEALING AND REGENERATION

[76] Inventors: Robert O. Becker, Box 278, Erie Canal Rd., Lowville, N.Y. 13367; A. Bartholomew Flick, 1 Lake Rabun Rd., P.O. Box 2088, Lakemont, Ga. 30552; Adam J. Becker, 2 Chateaux Cir., Apt. 2L, Scarsdale, N.Y. 10583

[21] Appl. No.: 623,046

[22] Filed: Mar. 28, 1996

[51] Int. Cl.$^6$ .................................................. A61M 5/32
[52] U.S. Cl. .............................................. 607/50; 604/20
[58] Field of Search ................................. 607/50; 604/20

[56] References Cited

U.S. PATENT DOCUMENTS

| | | |
|---|---|---|
| 3,799,162 | 3/1974 | Romero-Sierra . |
| 3,800,792 | 4/1974 | McKnight et al. . |
| 4,312,340 | 1/1982 | Donadelli . |
| 4,528,265 | 7/1985 | Becker .................................. 435/172.1 |
| 4,767,401 | 8/1988 | Seiderman . |
| 4,818,697 | 4/1989 | Liboff et al. . |
| 4,847,049 | 7/1989 | Yamamoto . |
| 4,932,951 | 6/1990 | Liboff et al. . |
| 4,937,323 | 6/1990 | Silver et al. . |
| 5,322,520 | 6/1994 | Milder . |
| 5,324,275 | 6/1994 | Raad et al. . |

OTHER PUBLICATIONS

R. O. Becker, et al., "Electrochemical Mechanisms and the Control of Biological Growth Processes," in Modern Aspects of Electrochemistry, No. 10, pp. 289–338, publ. Plenum Press (1971). USA.
R. E. Hall, et al., "Inhibitory and Cidal Antimicrobial Actions of Electrically Generated Silver Ions," J. Oral & Maxillofac. Surg., vol. 45, pp. 779–784 (1987). USA.
R. O. Becker, et al., "Experience With Low–Current Silver Electrode Treatment of Nonunion," in Electrical Prop. Bone & Cartilage (ed. C. T. Brighton, et al.), Grune & Stratton (1979), USA.
J. A. Spadaro, et al., "Experience With Anodic Silver in the Treatment of Osteomyelitis," 25th Ann. ORS Mtg., Feb. 20–22, 1979.
R. O. Becker, et al., "Treatment of Orthopaedic Infections With Electrically Generated Silver Ions," J. Bone & Joint Surgery, vol. 60–A, pp. 871–88 (1978). USA.
R. O. Becker, et al., "Clinical Exp. With Low Intensity Direct Current Stimulation of Bone Growth," Clin. Orthop. & Rel. Res., vol. 124, pp. 75–83 (1977) . USA.
T. J. Berger, et al., "Antifungal Properties of Electrically Generated Metallic Ions," Antimicrob. Agents & Chemother., vol. 10, pp. 856–860 (1976). USA.
T. J. Berger, et al., "Electrically Generated Silver Ions: Quantitative Effects on Bacterial & Mammalian Cells," Antimicrob. Agents & Chemother., vol. 9, pp. 357–358 (1976) USA.
J. A. Spadaro, et al., "Some Specific Cellular Effects of Electrically Injected Silver & Gold Ions," bioelectrochem. & Bioenergetics, vol. 3, pp. 49–57 (1976. USA.
J. A. Spadaro, et al., "Antibacterial Effects of Silver Electrodes With Weak Direct Current," Antimicrob. Agents & Chemother., vol. 6, pp. 637–642 (1974). USA.
M. R. Urist, et al., "Bone Morphogenesis in Implats of Insoluble Bone Gelatin," Proc. Nat. Acad. Sci. USA, vol. 70, No. 12, Part I, pp. 3511–3515 (1973). USA.

*Primary Examiner*—Scott Getzow
*Attorney, Agent, or Firm*—Maria Reichmanis

[57] ABSTRACT

An iontophoretic system for promoting tissue healing processes and inducing regeneration. The system includes a device and a method, a composition, and methods for making the composition in vitro and in vivo. The system is implemented by placing a flexible, silver-containing anode in contact with the wound, placing a cathode on intact skin near the anode, and applying a wound-specific DC voltage between the anode and the cathode. Electrically-generated silver ions from the anode penetrate into the adjacent tissues and undergo a sequence of reactions leading to formation of a silver-collagen complex. This complex acts as a biological inducer to cause the formation in vivo of an adequate blastema to support regeneration.

42 Claims, 11 Drawing Sheets
(7 of 11 Drawing Sheet(s) Filed in Color)

IONTOPHERETIC SYSTEM FOR STIMULATION OF TISSUE HEALING AND REGENERATION

BACKGROUND OF THE INVENTION

1. Field of the Invention

The present invention relates to an iontophoretic system for the stimulation of tissue healing and regeneration. In particular, the present invention relates to a method and device for stimulation of tissue healing and regeneration, a composition for use therewith, and methods for making the composition.

2. Discussion of Background

Healing, like all other biological processes, is a cellular process. The occurrence of an injury immediately triggers the onset of this process, which continues until the injury is healed. Although its exact mode of action is not yet understood, it is clear that a feedback mechanism monitors the extent of tissue damage and adjusts cellular activity in the injured area to produce the exact amount of healing needed.

As used herein, the terms "wound" and "injury" refer to tissue damage or loss of any kind, including but not limited to cuts, incisions (including surgical incisions), abrasions, lacerations, fractures, contusions, burns, and amputations.

Healing processes can be classified into three types, determined by how the cells in the injured area react to the injury. The simplest type of healing is scarification healing, wherein cells at the edges of a wound produce collagen and elastic fibers which simply bind the edges of the wound together without restoring severed nerves or blood vessels. This type of healing produces a visible scar, and sometimes results in numbness and circulatory inadequacy in the region of the wound and regions distal thereto. In the higher animals, including man, the heart, skeletal muscle, and nerve tissue (including the brain) heal by scarification.

A second type of healing is tissue replacement, wherein the cells of some body tissues produce more cells of their own kind to replace missing portions. In humans, the skin and portions of the gastrointestinal tract heal by replacement. In this type of healing, the replacement rate of the cells in the injured area increases to produce sufficient numbers of cells to help heal the injury, then returns to normal after healing is complete. Replacement is effective only if enough normal cells of the needed types are present in the area, and only for the particular types of cells that are capable of healing in this manner. Replacement is often inadequate for healing full-thickness skin wounds, which frequently heal with limited re-epithelialization, resulting in poorly innervated, thin and inelastic skin, while subcutaneous soft tissue defects heal primarily by scarification. However, such results are generally adequate for function if the wound is on the torso or the extremities (excepting the hand).

The most effective—and most complex—type of healing is regeneration. This type of healing is capable of replacing entire limbs and internal organs, and even portions of the brain and heart. Regeneration is a biphasic process. In the first phase, normal, mature cells at the site of the injury revert to an embryonic, unspecialized form ("de-differentiate"). These cells multiply rapidly, then become activated and demonstrate a variety of energetic processes which may include amitotic division, nuclear transfer, migration of free nuclei into residual tissues, and production of exceptionally large cells containing nuclear material from a number of individual de-differentiated cells (thus, "activated cells" are cells that undergo these processes). Activation results in the rapid accumulation of a large mass of embryonic cells known as the blastema, which is the essential element for regeneration. The blastema may be viewed as providing the biological raw material needed for rebuilding the missing tissues: formation of an adequate blastema results in complete regeneration of the missing tissues, whereas if the blastema is inadequate in size, only partial or incomplete regeneration takes place (formation of a stunted or incomplete part, or merely regeneration of individual tissue types that are not fully organized into the desired structure).

In the second phase of the regeneration process, the embryonic cells of the blastema respecialize ("re-differentiate") into the various types of cells needed to rebuild the missing tissues and organized structures in complete anatomical detail. The rebuilding process is essentially a recapitulation (albeit on a local scale) of the original embryonic development of the tissues being replaced.

In vertebrates, regenerative healing is found in certain species of amphibians (notably salamanders). It is almost totally lacking in humans, except in the fetus and in very young children (who may regenerate the distal finger tip if the wound is left open). In adults, regeneration is largely limited to parts of the fracture healing process. Clearly, it would be beneficial if humans could regenerate other damaged tissues, both in terms of more cost-effective treatment modalities and improved outcomes for patients.

The stimulus which initiates the complex regenerative process in amphibians has been reported to be a specific type of electrical signal, but the mechanism which provides the blueprint for the tissues to be regenerated is largely unknown. In the case of regeneration of individual tissues, however, a number of inducer substances that carry a specific signal causing either embryonic, de-differentiated, or mature cells to convert into specific tissue types have been identified. These "biological inducers" are analogous to chemical catalysts in that they effect cellular transformation by contact with the cells, but the inducer itself does not take part in the transformation. It is believed that biological inducers act by producing a signal in the nature of a specific electrical field which causes an event to occur on the surface of the target cell, which in turn causes the DNA in the target cell to alter the cell type in a specific fashion. By way of example, a "bone induction material" that causes the transformation of muscle cells into bone has been identified (M. Urist, *Proc. Nat. Acad. Sci. USA,* Vol. 70, pp. 3511–3515 (1973)).

Healing in general is known to be related to the degree of the injury, the amount of nerve tissue present at the site, and the electrical potential difference between the site and surrounding intact tissue (the "current of injury"). In particular, regeneration in amphibians such as salamanders and fracture healing in mammals are associated with complex changes in the local DC (direct current) electric field. An injury results in changes in the electric field and stimulates the animal's neural system, which in turn produces an electrical signal at the site of the injury, stimulating the complex cellular responses that eventually produce healing. The electric field gradually returns to normal, pre-injury levels as the injury heals. Conversely, failure of the normal healing process, as in fracture nonunions, is associated with the absence of appropriate electrical signals at the site of the injury.

These observations have lead to widespread use of electrical stimulation for the treatment of injuries in humans, especially fracture nonunions. Many studies have demonstrated that the application of small electrical currents (in the microampere range or lower) or weak magnetic or electric fields affects the growth or reunion of bone. See, for example, R. 0. Becker and A. A. Pilla, "Electrochemical Mechanisms and the Control of Biological Growth Processes," in *Modern Aspects of Electrochemistry* (ed. J. O'M. Bockris and B. E. Conway), Vol. 10, pp. 289–338 (1971); R. 0. Becker, et al., "Clinical Experiences With Low Intensity Direct Current Stimulation of Bone Growth," *Clinical Orthopedics & Related Research,* Vol. 24, pp. 75–83 (1977); R. 0. Becker & J. A. Spadaro, "Experience with Low Current Silver Electrode Treatment of Nonunion," in *Electrical Properties of Bone and Cartilage* (ed. C. Brighton, et al.), pp. 631–638 (1979); R. O. Becker, et al., "Clinical Experience with Low Intensity Direct Current Stimulation of Bone Growth," *Clinical Orthopedics and Related Research,* Vol. 124, pp. 75–83 (1977).

Furthermore, electrically-injected silver ions are known to have significant antibacterial and antifungal properties. Silver is a well-known antibiotic, widely used in topical applications in the form of silver nitrate solution, silver sulfadiazine, and so forth. However, the useful antibacterial effect of such compounds is limited and due only to the small amount of free silver ions produced by dissociation of the compound or to formation of toxic by-products (for example, use of silver nitrate ($AgNO_3$) solutions may lead to the formation of nitric acid). The antibacterial action of these ions is limited to a very localized effect directly on the wound surface.

Electrically-generated silver ions, on the other hand, penetrate at least approximately 1 cm into the wound and can be produced in much larger amounts than is possible with topical preparations such as silver sulfadiazine. Thus, electrically-injected silver is effective even against antibiotic-resistant strains, inhibiting bacterial growth in vivo and in vitro at current densities as low as 10 $nA/mm^2$ and concentrations as low as 0.5 mg/ml. Susceptible organisms include *S. aureus, E col.,* Candida and Torulopsis. These effects are described in a number of publications, including the following: J. A. Spadaro, et al., "Antibacterial Effects of Silver Electrodes with Weak Direct Current," *Antimicrobial Agents and Chemotherapy,* Vol. 6, pp. 637–642 (1974); J. A. Spadaro and R. 0. Becker, "Some Specific Cellular Effects of Electrically Injected Silver and Gold Ions," *Bioelectrochemistry and Bioenergetics, Vol. 3,* pp. 49–57 (1976); T. J. Berger, et al., "Antifungal Properties of Electrically Generated Metallic Ions," *Antimicrobial Agents and Chemotherapy,* Vol. 10, pp. 856–860 (1976); J. A. Spadaro and R. 0. Becker, "Experience With Anodic Silver in the Treatment of Osteomyelitis," *Proceedings of the 25th Annual Orthopedic Research Society Meeting,* Vol. 4, p. 10 (1979); R. 0. Becker, et al., "Treatment of Orthopedic Infections With Electrically-Generated Silver Ions," *Journal of Bone and Joint Surgery,* Vol. 60A, pp. 871–881 (1978).

At any particular silver concentration, electrically-generated silver ions are more effective in inhibiting bacterial growth than silver salts (T. J. Berger, et al., "Electrically Generated Silver Ions: Quantitative Effects on Bacterial and Mammalian Cells," *Antimicrobial Agents and Chemotherapy,* Vol. 9, pp. 357–358 (1976); Hall, et al., "Inhibitory and Cidal Antimicrobial Actions of Electrically Generated Silver Ions," *J. Oral and Maxillofac. Surg.,* Vol. 45, pp. 779–784, 1987).

Becker (U.S. Pat. No. 4,528,265) has disclosed processes and products that involve subjecting mammalian cells to the influence of electrically-generated silver ions. Anodic silver causes cells such as mammalian fibroblasts to assume a simpler, relatively unspecialized form and to resemble dedifferentiated or embryonic cell types. In mammals, including humans, this effect is associated only with the silver ions; the effect is not related to the electrical current or voltage. The afore-mentioned publications are incorporated herein by reference.

A variety of devices for use in electrical stimulation are known. Liboff, et al. disclose a noninvasive magnetic field generator for producing a controlled, fluctuating, directionally oriented magnetic field parallel to an axis projecting though the target tissue (U.S. Pat. No. 4,932,951). An externally-generated magnetic field can be combined with the local magnetic field to produce a resultant field that enhances transfer of ions such as $Ca^{++}$ across the membrane of a living cell (Liboff, et al., U.S. Pat. No. 4,818,697).

Other devices make use of the antimicrobial properties of silver and other metals. Raad, et al. (U.S. Pat. No. 5,324,275) disclose a catheter tube surrounded by two parallel helical conductors made of copper, gold, silver or other heavy metals. When connected to a DC power source such as a 9-volt battery, ions are transferred between the conductors through body fluids, and induce an antimicrobial effect proximate the area between the conductors.

Milder (U.S. Pat. No. 5,322,520) describes a material containing dissimilar metal powders, such as silver and gold, silver and copper, or silver and platinum mixed into a conductive polymer substrate. When contacted by an electrolytic solution, each metal granule that contacts the electrolyte becomes either an anode or a cathode, so the material contains an array of small batteries. Metal ions are driven into the solution to kill bacteria on and near a device to which the material is affixed. The material can be used in devices such as catheters, cardiac pacemaker leads, artificial hip joints, and so forth.

Seiderman (U.S. Pat. No. 4,767,401) describes a method for iontophoretic administration of medicaments such as silver protein (a colloid of silver with protein). The medicament is coated onto a metallic foil electrode so that, when in contact with a wound, natural body fluids and the negative electric charge of the wound site create a voltaic effect that causes the medicament to migrate into the wound.

Yamamoto (U.S. Pat. No. 4,847,049) and McKnight, et al. (U.S. Pat. No. 3,800,792) disclose collagen compositions used for wound treatment. Yamamoto contacts renatured collagen with a silver-ion-containing solution at pH between 4.0 and 9.0, forming a composition wherein silver ions are chelated to functional groups in the collagen. The composition is then exposed to UV radiation to strengthen the binding of the silver ions to the collagen. When the composition contacts bodily fluids, the silver ion is slowly released to protect the collagen from fungal and bacterial attack. McKnight's laminated collagen dressing is made from a layer of reconstituted collagen film laminated to a thin continuous layer of an inert polymer material such as polyurethane. Preferably, the collagen film contains finely divided silver metal particles, added by soaking the dried film in Tollen's reagent (($AgNH_3)_2OH$) for 5 minutes to oxidize excess glutaraldehyde and deposit silver metal on the accessible surfaces of the collagen fibers.

Silver, et al. (U.S. Pat. No. 4,937,323) dress a wound with a biocompatible, biodegradable collagen product and apply low intensity direct current in the range of 10–100 microamperes. The collagen product may be a sponge made of collagen powder or flakes, and contains electrodes made of carbon or metal inserted therein. Donadelli (U.S. Pat. No.

4,312,340) treats scarred skin using a solution containing embryonic placenta, collagen and vitreous humor extracts diluted in distilled water, treated by partial electrolysis to provide a formation of groups of amino acids. A variable low frequency electric field is applied to create an electric charge below the scarred area. Romero-Sierra, et al. (U.S. Pat. No. 3,799,162) apply histamine to a lesion, and then radiate the cells bounding the lesion with low intensity nonionizing electromagnetic radiation to stimulate production of collagen at the site.

Despite the wide variety of known treatment modalities, no known treatment produces sufficient numbers of the de-differentiated (i.e., embryonic) cells required for true regeneration in humans and other mammals. In fact, the treatment of injuries involving traumatic loss of skin and soft tissue, particularly for hand injuries, ranges from judicious neglect to major surgery. In the case of hand injuries, the twin requirements of flexibility and sensation mean that the above-described natural and enhanced healing processes are inadequate to yield good functional results.

There is a need for a flexible, effective system that helps promote and enhance tissue healing processes in mammals, including humans. Use of such a system would not only improve the outcome of the processes responsible for most healing in humans (scarification, tissue replacement), but would, in appropriate instances, induce true regenerative healing resulting in regrowth of the specific tissue types appropriate to the situs of the injury (normally innervated, full thickness skin, subcutaneous soft tissues, bone, etc.). The system would make use of simple, efficient delivery devices, be safe and easy to use, and be capable of being applied directly to the wound site.

SUMMARY OF THE INVENTION

According to its major aspects and broadly stated, the present invention is an iontophoretic system for promoting tissue healing processes and inducing regeneration. The system includes a device and a method, a composition, and methods for making the composition in vitro and in vivo. The system is implemented as follows: a flexible, silver-containing anode is placed in contact with the wound, a cathode is placed on intact skin near the anode, and a wound-specific DC voltage is applied between the anode and the cathode.

Electrically-generated silver ions from the anode penetrate into the adjacent tissues and undergo a series of three reactions. First, the silver ions combine with proteins, peptides and various other chemical species normally present in solution in the tissues. The silver ions also combine with any bacteria, fungi or viruses present in the treatment area. If treatment is continued after all or most available sites for this type of reaction have been exhausted, the newly-generated silver ions associate with cells in the region, particularly fibroblast cells and epithelial cells, resulting in de-differentiation of these cells into embryonic cell types. Then, if treatment is continued after this second reaction is substantially complete, the free silver ions form a complex with collagen fibers present in the wound. This silver-collagen complex is believed to act as a biological inducer to activate the previously-produced de-differentiated fibroblast or epidermal cells to multiply and produce an adequate blastema.

In mammalian-including human-wounds treated at appropriate, wound-specific voltages, for a sufficient period of time to carry out the above-described reactions, and with anodes capable of supplying a sufficient number of silver ions for these reactions to take place, the resulting effects are analogous to those observed in animals that are naturally capable of regeneration. That is, the activated de-differentiated cells rapidly multiply to form a blastema that is adequate for supporting regeneration of the missing or injured tissues (skin, subcutaneous tissues, bone, and so forth).

A major feature of the present invention is the scaling of the applied voltage to the size of the wound. Surprisingly, an approximately constant voltage on the order of 0.1 V/in$^2$ of wound area (about 0.0155 V/cm$^2$) has been found to be optimum for promoting healing and regeneration of tissues while substantially avoiding the deleterious effects associated with biological electrolysis (to be described further below). Not only are specific voltages in this range remarkably effective in stimulating tissue healing and regeneration, but the electrically-injected silver ions are extremely effective against a wide variety of bacterial types (including gram positive, gram negative, aerobic and anaerobic forms), fungi, and local viral infections. Therefore, under optimal treatment conditions, the electrically-injected silver ions are an extremely effective agent against mixed infections and against many antibiotic-resistant strains.

An important feature of the invention is the anode, which is made of a material having a sufficiently high silver content to supply the needed silver ions to the wound. The anode is made of a flexible, silver-containing material that is conformable to the wound surface, such as silver-coated nylon fabric or the like. Materials usable with the invention contain a sufficient quantity of silver to produce an approximately constant current into the treated area for at least several hours, preferably 12–24 hours or thereabouts. Thus, silver-containing fabrics with a low specific resistance are needed, preferably fabrics having a specific resistance no greater than approximately 5 $\Omega$/cm, preferably no greater than approximately 1 $\Omega$/cm. Furthermore, fabrics with an approximately uniform silver content (i.e., a uniform silver content per unit area) that produce a uniform specific resistance throughout the electrode are preferred. Other metals (gold, copper, zinc, and so forth) may also be effective.

Another feature of the invention is the cathode, which, like the anode, is made of a flexible, electrically-conducting material, preferably a material having a specific resistance no greater than approximately 500 $\Omega$/cm. By way of example, the cathode may be made of carbon rubber or like materials.

Still another feature of the invention is the placement of the cathode. For optimum results, the cathode is placed so as to achieve an approximately uniform flow of current through the treated region. In the human body, current tends to follow the shortest path from the anode to the cathode. Therefore, whenever possible, the cathode is positioned on the opposing side of the extremity being treated from the wound: for wounds on the palm of the hand, the cathode is placed on the back of the hand; for wounds on the dorsal surface of the forearm, the cathode is positioned on the ventral surface, and so forth.

Another feature of the invention is the silver-collagen complex, a specific physical association of the electrically-injected silver ions with the collagen fibers present in the wound area. While not wishing to be bound by theory, it is believed that this complex generates a unique localized electric field that activates embryonic cells in the treated area, eventually leading to formation of an adequate blastema to support regeneration.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

This application contains color drawings.

In the drawings.

DETAILED DESCRIPTION OF PREFERRED EMBODIMENTS

Figure 1:
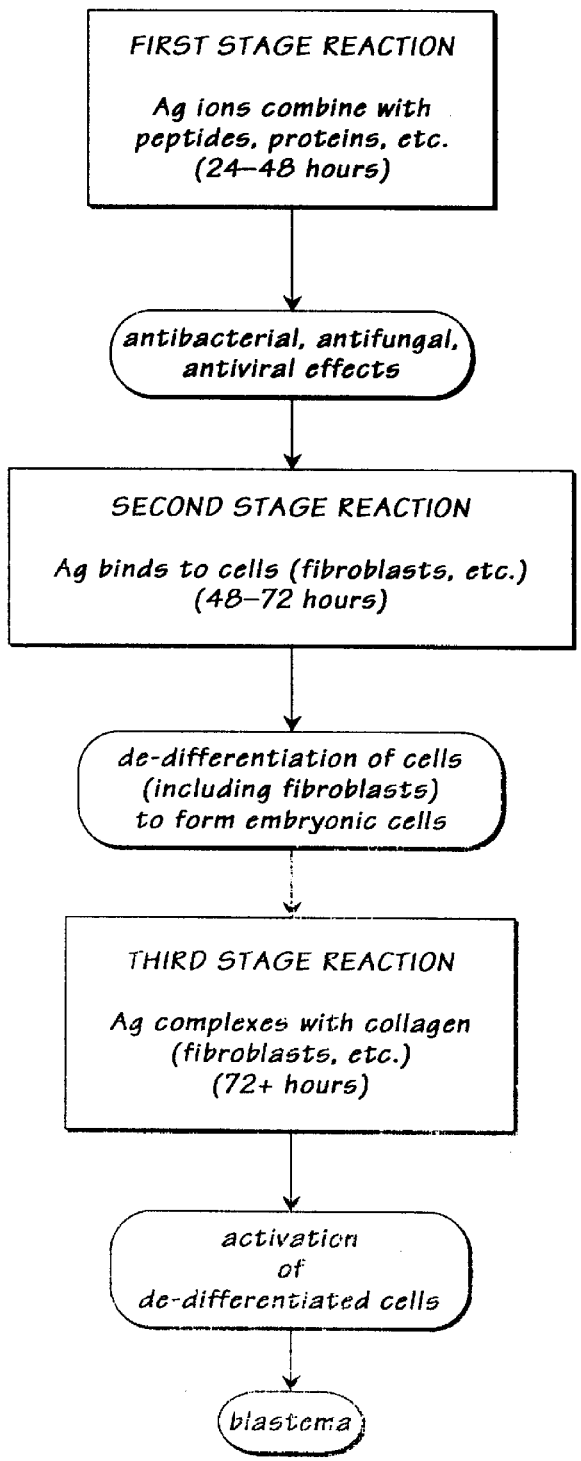
FIG. 1 is a flow chart showing three sequential reaction processes resulting from the action of electrically-injected silver ions.

In the following description, like reference numerals refer to and identify the same structural elements, portions or surfaces consistently throughout the drawings, as such elements, portions or surfaces may be further described or explained by the entire written specification. The terms "proximal," "distal," "dorsal," "ventral," "volar," "opposing," "anterior" and "posterior" are used in the customary anatomical sense. The "size" or "surface area" of a wound or injury means the approximate surface area on a macroscopic scale. The terms "scaled voltage" and "specific voltage" refer to the voltage per unit surface area, for example, V/cm$^2$ or V/in$^2$. Similarly, the term "specific resistance" means the resistance per unit surface area.

A number of critical factors have been identified that are required for the successful use of silver iontophoresis techniques to promote tissue healing and regeneration. These factors are as follows:

1. There is a critical, previously unsuspected relationship between the size of the wound and the optimum magnitude of the voltage applied across the anode and the cathode. Electrical injection of silver ions using an approximately constant DC voltage scaled to the size of the wound is surprisingly effective in promoting healing and regrowth of injured and missing tissues. Treatment is accomplished by placing a flexible, silver-containing anode in contact with the open surface of the wound, placing a cathode in contact with intact skin near the wound, and applying an appropriate DC voltage, generally for at least approximately 24 hours.

2. The silver content of the anode should be high enough to ensure a low specific resistance, preferably a specific resistance no greater than approximately 5 Ω/cm, more preferably no greater than approximately 1 Ω/cm. Anodes with higher specific resistances may also be useful for the practice of the invention however, the optimum effect is achieved with low-resistance anodes. In addition, the silver should be approximately uniformly distributed (that is, the amount of silver per unit surface area of the anode should be approximately uniform).

3. The cathode should be a flexible material capable of making and maintaining a low resistance contact with intact skin, so that the combined specific resistance (i.e., cathode resistance and contact resistance) is no greater than approximately 500 Ω/cm.

4. The cathode should be positioned to maximize current flow into the wound.

5. To maximize the input of silver ions into the wound, the current should be maximized by minimizing the total circuit resistance.

When these critical factors are present, an unexpected phenomenon occurs: the input of sufficiently large numbers of silver ions during a biologically appropriate time frame (within 3–5 days) enables formation of a complex between the silver ions and the collagen fibers in the wound. This silver-collagen complex acts as a biological inducer to cause the continual de-differentiation of fibroblast cells and the continual multiplication of previously de-differentiated cells in the area of the wound, leading to the accumulation of many more embryonic cells in the area and, eventually, formation of an adequate blastema to produce regeneration. These factors will be discussed more fully below.

Scaling the applied DC voltage to the size of the wound is crucial to successful treatment. The voltage should be high enough to ensure an adequate input of silver ions into the wound, but not so high that the deleterious effects caused by biological electrolysis become evident. "Biological electrolysis" or electrolysis in vivo differs from electrolysis in vitro in the following respects: electrolysis occurs in living tissues whenever there is current flow, no matter how small. However, a wide variety of naturally occurring agents act as buffers to prevent the accumulation of potentially harmful electrolysis products. These products are continually removed by blood and lymphatic circulation (which also ensures a continual supply of fresh buffers), thereby preventing a buildup of electrolysis products in the area. If the critical voltage is exceeded, this natural buffering action is rapidly overwhelmed and electrolysis products accumulate with attendant pH shifts. This point defines the onset of "biological electrolysis," which can be avoided by taking the above-described critical values of voltage/area into consideration.

Thus, selection of the appropriate treatment voltage requires a knowledge of what happens in living tissue, where the effects of electrolysis can be overcome by circulation and buffering factors up to a point. The effects of naturally-occurring buffers, blood circulation and lymph circulation depend on the size of the wound. Thus, the results of in vitro testing do not apply, nor do in vivo observations of only one size of wound—each wound has its own maximal voltage range which has to be clinically determined.

The critical specific voltage has been determined to be approximately 0.09–0.11 $V/in^2$ (about $1.4\times10^{-2}$–$1.7\times10^{-2}$ $V/cm^2$), preferably approximately 0.1 $V/in^2$ (about $1.55\times 10^{-2}$ $V/cm^2$). Not only are specific voltages in this range surprisingly effective in promoting tissue healing and regeneration, but the electrically-generated silver ions are extremely effective against a wide variety of bacterial types, including gram positive, gram negative, aerobic and anaerobic forms. Similar effects have been noted against a number of common fungi that colonize open wounds, and may also occur in a number of local viral infections (including herpes). Therefore, under optimal treatment conditions, silver ions are an extremely effective agent against mixed infections and against many bacteria that have become antibiotic-resistant.

For any given size of wound, voltages lower than optimum have no undesirable effects, but simply reduce the efficacy of treatment in an approximately linear fashion due to the production of fewer silver ions during any given period of time, and more limited electrophoretic migration of those ions into the tissues. At sufficiently low voltages, it is simply not possible to supply enough silver ions in the time frame required to produce the desired effects.

Higher voltages result in undesirable effects, also in an approximately linear relationship to the applied voltage. These effects range from irritation and slower healing at modest overvoltages to localized pH alterations due to accumulation of electrolysis products, cellular necrosis, and actual increases in wound size at higher overvoltages. The resulting buildup of dead tissue shields bacteria, fungi, etc. in the region from the silver ion action and limits the penetration depth of the ions.

Use of the appropriate anode material contributes to a uniform current/voltage distribution over the treatment area, together with a longer use time before the onset of polarization. Preferably, the anode is made of a flexible material with an approximately uniform silver content, for example, flexible, silver-containing fabric. In practice, the anode is replaced daily, thus, anode materials which are capable of supplying a sufficient quantity of silver ions for approximately 24 hours are preferred. Therefore, the silver content of the anode is preferably sufficient to yield a specific resistance no greater than about 1 $\Omega/cm$, as noted above. Anodes with somewhat higher resistance (lower silver content) may also be useful; however, these will be exhausted in shorter periods of time, necessitating more frequent replacement. Furthermore, higher-resistance anodes may lead to non-linear voltages and thereby reduce the efficacy of treatment.

The anode should also not only have a sufficiently high content of silver (or other suitable metal; see below), but the silver should be approximately uniformly distributed. Non-uniform distribution means that the wound will not be uniformly treated: some localized areas may be subjected to significantly higher specific voltages that others and the number of silver ions supplied to different areas will differ. In some such instances, the local specific voltage may be high enough to cause toxic effects.

It will be understood by those skilled in the art that suitable anode materials may include those containing silver alloys as well as substantially pure silver. Other metals that produce the desired results may also be usable in the practice of the invention, for example, gold, copper, platinum, zinc, and so forth.

Suitable cathode materials include flexible carbon rubber or the like (preferably containing the maximum possible amount of carbon or graphite), or carbon-filled or metal-containing fabric, having a specific resistance no greater than approximately 500 $\Omega/cm$.

Optimum cathode placement is determined by current flow in the human body. Current tends to follow the shortest path from the anode to the cathode (i.e., the body cannot be viewed as a single volume conductor). Therefore, part or all of the wound will not be adequately treated if cathode placement is nonoptimum. For example, for wounds on the palm of the hand, placement of the cathode on the wrist results in more silver ions being delivered to the proximal portion of the wound and frequently an inadequate amount to the distal portion. A more uniform distribution is achieved by placing the cathode on the opposite side of the hand (the dorsum), directly opposed to the palmar wound.

Optimal treatment according to the present invention has as its aim the continuous introduction of the largest possible population of silver ions into the wound until healing or regeneration is complete, in a fashion that does not introduce harmful by-products or produce deleterious effects on the cellular processes. As noted above, the total circuit resistance is minimized—and the current maximized—in order to maximize the number of silver ions delivered to the treatment site. The current may be monitored to ensure that there are no high-resistance areas in the circuit (for example, a dry treatment electrode, loose cathode, and so forth).

When introduced into living tissues, electrically generated silver ions undergo a series of three reactions in a sequential fashion (FIG. 1):

In the first reaction, the silver ions combine with proteins, peptides and other chemical species normally present in solution in the tissues. Further chemical or physiochemical combinations do not occur until all such simple sites are completely filled. The first reaction typically requires approximately 24 hours to go to completion (wherein the term "completion" refers to saturation of available sites). The antibacterial action of silver ions is a result of this type of process, beginning at about 20–30 minutes following exposure of the bacteria to the ions.

If more free silver ions are made available following the first reaction, the second reaction occurs. The second reaction is an association between the silver ions and sensitive cells present in the wound, resulting in de-differentiation of these cells into embryonic cell types (as used herein, the term "sensitive cells" refers to cells that are sensitive to free silver ions, including, among others, mature fibroblast cells and epithelial cells). These embryonic cells are not activated in the sense that they do not multiply to produce additional cells of the same type; however, they are capable of re-differentiation into other cell types. Hence, these cells do not form an adequate blastema mass to produce organized, multi-tissue regeneration. Production of de-differentiated fibroblasts requires a continuous supply of excess silver ions for at least approximately 48–72 hours following saturation of the active chemical sites in the first reaction ("excess" in this context means that more silver ions are supplied than are needed to combine with all available proteins, peptides, etc. in the above-described first reaction).

If sufficient silver ions are made available after the second reaction, a third reaction begins to take place. The third reaction constitutes a specific physical association of at least some of the silver ions with the collagen fibers present in the wound to produce a unique structure ("silver-collagen complex") having the specific properties required to induce activation of the de-differentiated fibroblast cells previously produced in the second reaction.

Collagen fibers have size-specific sites which are capable of forming a complex with hydrated metallic ions (J. A.

Spadaro, et al., "Size-Specific Metal Complexing Sites in Native Collagen," *Nature,* Vol. 225, pp. 1134–1136 (1970)). The copper/collagen complex, in particular, has a unique electrical field which is involved in the initial epitaxial deposition of bone mineral (apatite) on bone collagen (A. A. Marino, et al., "Evidence of Epitaxy in the Formation of Collagen and Apatite," *Nature,* Vol. 226, pp. 652–653 (1970)). While not wishing to be bound by theory, it is believed that a silver-collagen complex according to the present invention has a unique local electrical field, and acts as a biological inducer to activate the de-differentiated fibroblast cells formed in the above-described second reaction. In mammalian wounds (including human wounds) treated at appropriate specific voltages with an excess of electrically generated silver ions, the formation of this silver-collagen inducer complex results in activation of the de-differentiated embryonic cells formed by the action of the silver ions on the pre-existing mature cells. Together, these effects result in cell behavior and action akin to those observed in animals that are capable of regeneration. In this fashion, an adequate blastema to support regeneration is formed in human tissue.

The above-described factors are designed to maximize the amount of silver ions introduced into the wound during the window wherein the above-described reactions can occur and lead to the formation of an adequate blastema for regeneration—a necessary condition for completing the sequence of three reactions within a biologically appropriate time. Of these factors, the first (scaling the applied voltage to the size of the wound) is believed to be crucial. If too few silver ions are provided, healing simply proceeds according to normal (i.e., nonregenerative) processes. Lower-than-optimum voltages reduce the efficiency of the treatment and lead to eventual failure of regenerative healing (although healing by scarification and tissue replacement will still occur). Higher-than-optimal voltages inhibit the third reaction (formation of the silver/collagen complex) due to pH shifts, accumulation of electrolysis products, tissue necrosis, and expansion of wound size.

Figure 2:
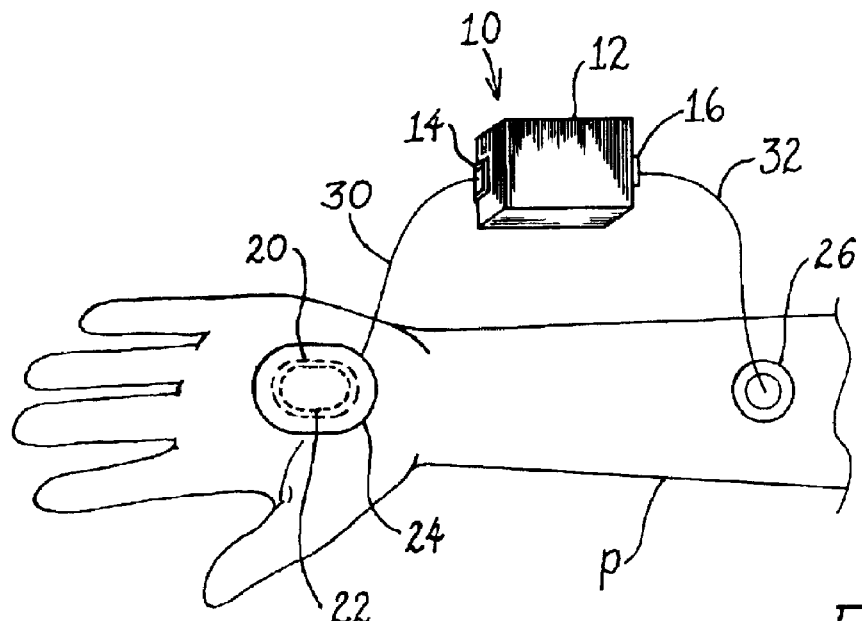
FIG. 2 shows an electrical stimulation device in use.

Referring now to FIG. 2, there is shown a schematic view of an electrical stimulation device in use. A device 10 includes a DC power source 12 with a positive terminal 14 and a negative terminal 16. A treatment electrode or anode 20 is placed in contact with the surface of a wound to be treated, for example, a full-thickness defect 22 on the palm of a patient P. Anode 20 is made of a flexible, metal-containing material, preferably a flexible metal-containing fabric such as silver-impregnated or silver-coated nylon. Anode 20 may be covered by a "stent" of gauze moistened with normal saline and a cover (such as plastic film or like material), represented as 24. A return electrode (cathode 26) is placed in contact with intact skin near wound 22, for example, proximal to wound 22 as shown. Anode 20 and cathode 26 are connected to power source 12 by cables 30, 32, respectively. If desired, cathode 26 may be incorporated into power source 20, for example, attached to one side of the power source.

Figure 3:
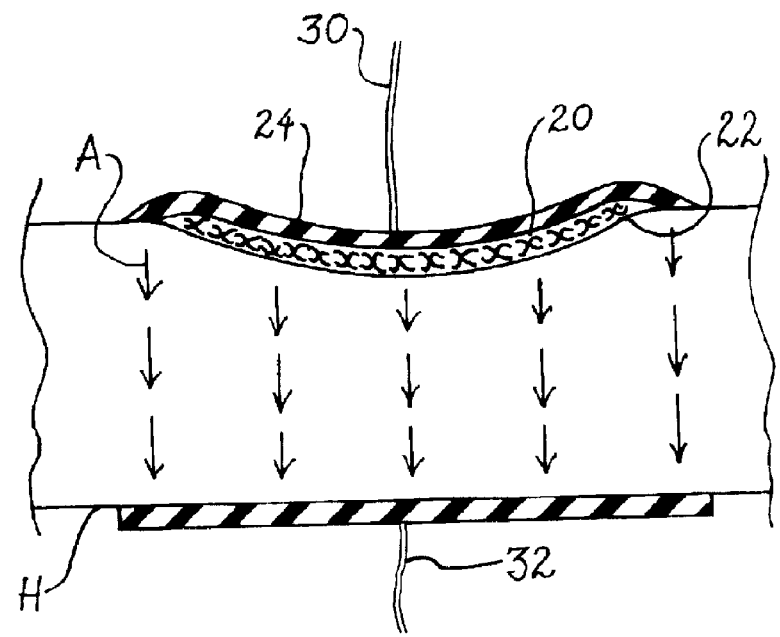
FIG. 3 shows the preferred placement of the cathode for optimum treatment according to the present invention.

While treatment with the system shown in FIG. 2 may be helpful, current flow (and, therefore, the supply of silver ions) to wound 22 is not optimized by the placement of cathode 26. As described above, the preferred placement of cathode 26 is one that results in an approximately uniform distribution of current through the wound, thereby ensuring approximately uniform delivery of silver ions thereto. Optimum placement of cathode 26 is on the opposite side of the body from the wound being treated, as illustrated in FIG. 3. For a wound 22 on a surface 44 of the body (for example, the palm of the hand), anode 20 is placed in contact with the wound, and cathode 26 is placed on an opposite surface 46 (for example, on the surface directly opposed to the palm). This placement ensures an approximately uniform distribution of current flow through wound 22, indicated schematically by arrows 48.

Figure 4:
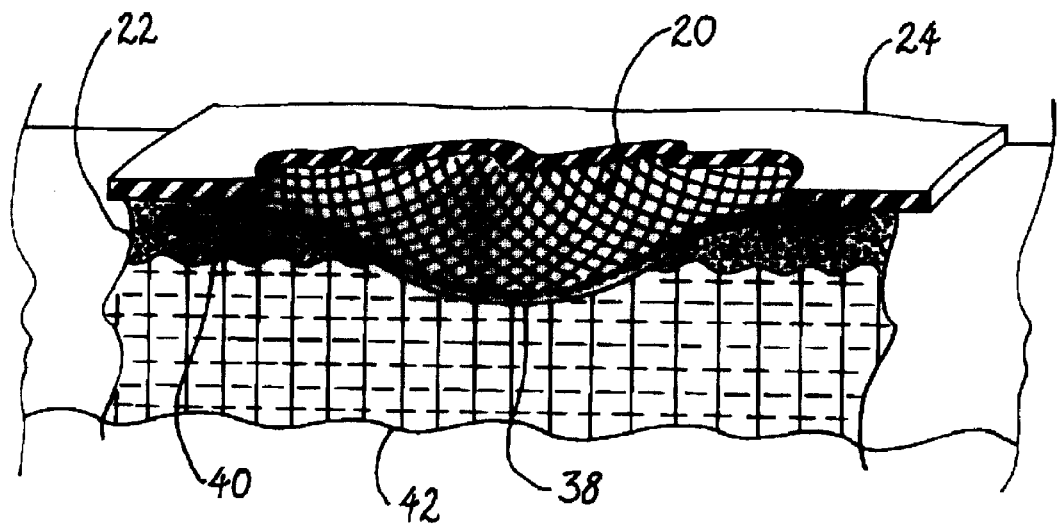
FIG. 4 is a partially cut-away view showing a silver-containing anode placed on the surface of a wound.

For optimum treatment, anode 20 substantially engages a surface 38 of wound 22, as shown in FIGS. 3 and 4. The presence of void spaces (even if filled with conducting solution) results in inadequate treatment at those points. Depending on the extent of wound 22, anode 20 may be in contact with exposed subcutaneous tissues 42 as well as dermal tissue 40 at the margins of the wound. Thus, the material of anode 20 needs to be sufficiently flexible to conform to surface 38. As shown in FIG. 4, anode 20 is dimensioned to just cover wound 20, that is, anode 20 has a slightly larger surface area than the area of wound surface 38.

Figure 5:
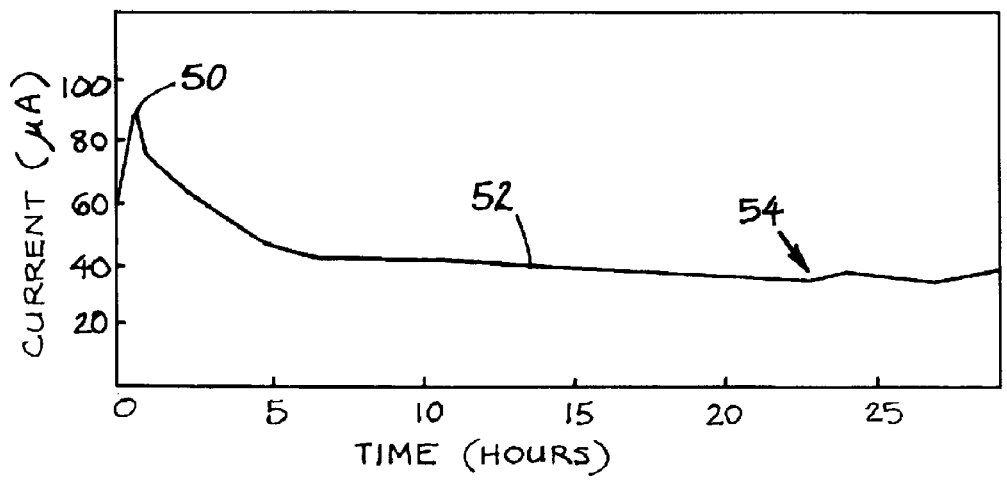
FIG. 5 is a plot of the current vs. time for a silver-containing material usable with the present invention, measured in vitro.

As described above, anode 20 contains a sufficient quantity of silver so that, when device 10 is connected for use as shown in FIG. 2, the current density delivered to wound 22 is approximately constant for a period of several hours, preferably at least approximately 24 hours. By "approximately constant current" is meant a DC current that may increase to a peak 50 immediately after the onset of treatment, but that decreases within several hours to an approximately constant level 52 and maintains that level until the onset of polarization at 54 (FIG. 5). FIG. 5 shows the current vs. time in vitro for a 25 cm$^2$ section of a silver-coated nylon fabric usable with the invention, applied to a block of gelatin prepared with physiological saline. A standard return electrode was applied to the opposite face of the block and a voltage of 0.42 V applied between the two electrodes. The current density at peak 50 was approximately 3.5 $\mu$A/cm$^2$, decreased to approximately 1.5 $\mu$A/cm$^2$ within 5 hours, and remained at that level until the onset of polarization approximately 20 hours later.

Figure 6:
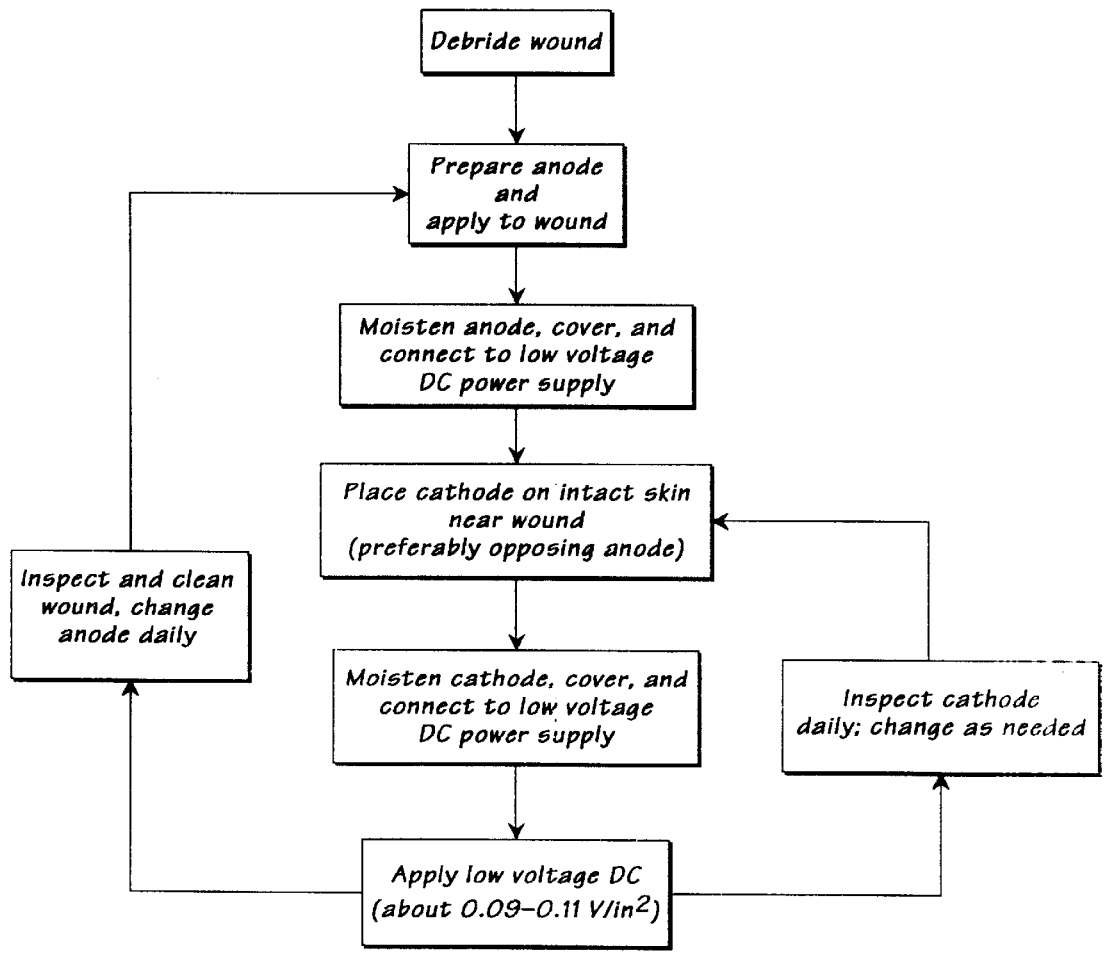
FIG. 6 is a flow chart illustrating treatment according to a preferred embodiment of the present invention.

A flow chart illustrating treatment according to the present invention is shown in FIG. 6. Patients are treated as soon as possible following the injury, preferably immediately following cleaning and debridement (if needed) of the wound. However, treatment may be initiated at any time thereafter, or whenever deemed medically necessary. The treatment electrode (anode 20) is applied directly to the surface of the wound, moistened with physiological saline or other suitable liquid, covered, and connected to the positive terminal of a low-voltage DC power source (such as source 12). The return electrode (cathode 26) is placed on intact skin near the wound (on an opposing surface whenever possible) and connected to the negative terminal of the source. Then, a low intensity DC voltage and current are applied continuously for a period of at least approximately 24 hours. The wound is inspected and cleaned daily, and anode 20 is replaced at that time. Cathode 26 is inspected daily and changed as needed.

Liquids suitable for use with the invention include electrically conducting liquids such as normal saline (also known as isotonic saline or physiological saline), Ringer's solution, wound exudate and other body fluids found in the area of the wound, and mixtures and dilutions thereof. Tap water may also be useful; however, the composition of tap water is so variable that other electrically-conducting liquids are preferred. The terms "normal saline," "isotonic saline" and "physiological saline" refer to a solution of sodium chloride (NaCl) in purified water (H$_2$O), containing approximately 0.9 gram of sodium chloride per 100 milliliters of water. Such a solution is approximately isotonic (i.e., has the same osmotic pressure) with body fluids. The term "Ringer's solution" means a solution of about 0.86 gram sodium chloride (NaCl), 0.03 gram potassium chloride (KCl), and 0.033 gram calcium chloride (CaCl) in purified water. The term "wound exudate" refers to any substance that is exuded from a wound, including materials that pass through the walls of blood vessel walls into the surrounding tissues.

The key element in promoting healing and regeneration according to the present invention is the production of de-differentiated cells in the region of the wound, which in turn depends on the above-described critical factors. The voltage applied across the treatment (anode 20) and return (cathode 26) electrodes must be wound-specific, that is, proportional to the size of the wound (preferably, approximately 0.1 V/in$^2$); the anode must have an approximately uniform silver content that is sufficiently high to ensure a specific resistance no greater than approximately 1 $\Omega$/cm; the cathode must be made of a suitable low-resistance material capable of making and maintaining a low resistance contact with intact skin; the cathode is positioned so as to maximize current flow into the wound insofar as practicable; the total circuit resistance is as low as possible. In all instances, the treatment electrode is configured so as to yield an approximately uniform voltage distribution throughout the area of the wound.

Scaling the voltage to the size of the wound is particularly important in the case of larger wounds (that is, wounds with surface areas greater than approximately 8–10 in$^2$ (about 50–65 cm$^2$), where a naonuniform voltage distribution through anode 20 may result in the production of electrolysis effects in localized "hot spots."

In all cases, the total voltage applied across anode 20 and cathode 26 is preferably no greater than about 0.9–1.1 V. The the area of anode 20—and the size of a wound treated therewith—is therefore limited to approximately 9–11 in$^2$ (about 60–70 cm$^2$). For larger wounds, two or more devices 10, each with its own anode, cathode, etc. are used, thereby ensuring that no single anode-cathode pair has an applied voltage greater than the preferred maximum. Thus, power source 12 may have several output voltages, each with a corresponding output terminal (for example, 0.1 V, 0.2 V, and so forth) for treatment of wounds of the corresponding size. Anodes 20 for use with such a power source have terminals that allow them to be connected only to the output terminal with the correct output voltage: a 1"-square anode to the 0.1V terminal, a 2"-square anode with the 0.2V terminal, and so forth.

During treatment, silver ions from anode 20 migrate into the tissues surrounding wound 20, where the ions undergo the three reactions shown in FIG. 1: binding to proteins, peptides, etc. in the area; de-differentiation of normal cells (primarily fibroblasts) into primitive, de-differentiated cells, and binding to collagen fibers to form a silver-collagen composition that in turn activates the de-differentiated cells. The activated cells multiply rapidly and re-differentiate to form the specific types of normal mammalian cells needed to restore the region to its pre-injury state (dermal and epidermal tissue, muscle tissue, nerve tissue, blood vessels, bone cells, and so forth, as may be needed for the particular site being treated).

As noted above, silver compounds such as AgNO$_3$ have long been known to possess bactericidal and fungicidal properties; however, compounds of the higher oxidation states of silver (Ag(II) and Ag(III)) have recently been found to be significantly more effective than monovalent (Ag(I)) compounds (M. S. Antelman, "Silver (II,III) Disinfectants," Soap/Cosmetics/Chemical Specialties, March, 1994, pp. 52–59). While not wishing to be bound by theory, it is thought that the superior bactericidal and fungicidal effects of electrically-generated silver ions may be due at least in part to the formation of free silver ions of these higher oxidation states and their action on bacteria, fungi, etc. present in the tissues.

It is believed that the silver-collagen complex formed at the treatment site results from a specific attachment of silver ions to collagen fibers, resulting in the formation of electrically active sites which act as biological inducers to activate the de-differentiated fibroblast cells. The complex may also have a de-differentiating effect on at least some of the remaining silver-sensitive cells in the area, but without requiring the direct attachment of the silver ion to the cell membrane as in the second reaction (FIG. 1). Thus, optimum treatment conditions result in a greater immediate effect on the cellular components in the wound area than do silver ions alone, since a much greater number of active de-differentiated cells are produced than would result solely from the direct action of electrically-introduced silver ions on the fibroblast cells. The complex also permits the expression of additional long term healing and maturational effects after active silver treatment is terminated, as will be described further below.

The silver-collagen complex may be prepared in vitro by application of low-voltage DC current from a silver anode to a collagen-containing substrate, then formed into suitable shapes (rolls, sheets, etc.) for external application to surface wounds or internal application to body parts (if desired, the complex may be incorporated into a wound dressing). The complex may act to produce de-differentiation of mature, sensitive cells; alternatively it may activate previously de-differentiated cells in the area. For applications where there are insufficient numbers of mature fibroblast cells present, the complex may be infiltrated with de-differentiated cells produced by the above-described technique in order to provide a source of de-differentiated cells to start the in vivo induction process.

The present invention is further illustrated in the following nonlimiting examples.

EXAMPLE 1

Portions of granulation tissue ranging in size from approximately 1–2 mm were removed from optimally treated wounds and explanted into an appropriate tissue culture medium, resulting in the formation of large numbers of new cells in the culture medium. The new cells were embryonic in nature and formed in contact with the explants, multiplying rapidly and spreading out from the explants until approximately ¾ of the culture dish was covered with embryonic cells. New cell formation ceased after 3–4 weeks, and all the cells then present reverted to normal fibroblast morphology. No further cell multiplication occurred.

EXAMPLE 2

Explants of granulation tissue were cultured as described in Example 1; however, the original explants were removed from the culture medium before cessation of new cell formation. All new cell production ceased after removal of the explants from the culture medium. Histological analysis revealed that the explants removed from the culture medium were composed solely of collagen fibers.

EXAMPLE 3

Explants of granulation tissue were cultured as described in Example 1. The explants were removed from the culture medium at approximately 1-week intervals, placed in sterile saline and refrigerated for 3–5 days. All new cell production ceased after removal of the explants from the culture medium; cell production resumed after the explants were re-implanted in the medium.

EXAMPLE 4

Granulation tissue from a wound treated with a specific voltage greater than the above-described optimum was explanted into a suitable tissue culture medium. No new cell production was observed, regardless of the length of time the culture was maintained.

EXAMPLE 5

Granulation tissue from an optimally treated wound was maintained in tissue culture until the cessation of new cell formation, but before reversion of the embryonic cells to mature fibroblasts. The explanted granulation tissue was removed, injected with silver ions for approximately two hours, and then re-implanted into the original culture medium at its original site. New cell production resumed.

EXAMPLE 6

Gelatin blocks were prepared from commercial collagen product in a normal saline solution. After hardening, the blocks were subjected to appropriate levels of DC voltage from a silver anode for 12 hours. After cessation of electrical treatment and removal of the anode, the blocks demonstrated a voltage and current production only slightly lower than that administered for an additional 10–12 hours.

While the exact structure of the silver-collagen complex has not been determined, Examples 1–6 indicate the production of such a complex under the appropriate conditions (i.e., when wounds are treated with the optimum specific voltage). The complex does not form when wounds are subject to higher voltages.

EXAMPLE 7

Volunteer patients were treated for a wide variety of traumatic wounds using the above-described methodology, including wounds to the extremities which may heal with difficulty due to poor natural healing processes. Each patient was advised of the experimental nature of the treatment and was offered conventional treatment; each patient who selected the experimental treatment was free to discontinue it at any time. Treated wounds included burns, lacerations, crush injuries, amputations, and infections. Patients ranged in age from 2.5 years to 81 years.

Patients were treated as soon as possible following the trauma. Debridement, if needed, was done under anesthesia. Silver ions were introduced directly into the wound by means of a small electrical current from a silver-containing nylon anode as described above. The treatment electrode (anode 20) was cut to approximately fit the wound, wetted with tap water and/or normal saline, and applied directly to the wound. The electrode was then covered with a small flexible, carbon-rubber electrode with an integral, thin, flexible wire that was connected to the anode of a DC power source. The wound was then wrapped in a soft dressing with a water-impermeable layer to prevent the dressing from drying out.

The return electrode (cathode 26) was placed on the opposing side of the limb from the wound as indicated in FIG. 3. Where this placement was not feasible (for example, fingertip injuries), the return electrode was placed proximal to the wound as shown in FIG. 2. The power source was a voltage-controlled, battery operated solid state unit set to deliver a constant, direct current voltage.

Most patients were treated on an outpatient basis after the patient and his/her family members were instructed in the techniques of electrode preparation and application. Treatment was continuous; the anode was changed daily with no special sterile precautions. The cathode was removed daily, cleaned with tap water and reapplied to the original site. All patients continued their daily dressing changes at home with weekly follow-up visits; all reported minimal difficulty or pain associated with the dressing changes. Patients with obviously contaminated wounds were given systemic antibiotics for the initial three days of treatment to prevent systemic infection (for example, infection resulting from any initial surgical debridement). No infections occurred in the entire series; all pre-existing infections cleared rapidly (within 3–4 days). Patient compliance was excellent, and treatment was terminated when a satisfactory clinical result was achieved.

A total of 24 wounds were treated, including burns, lacerations, crush injuries, open fractures, amputations, and infections. All wounds involved soft tissue loss with full thickness skin loss ranging in area from 1 cm$^2$ to 18 cm$^2$ with an average of about 4 cm$^2$. Treatment voltages ranged from about 0.3 V to about 0.9 V, depending on the surface area of the wound. Current densities ranged from approximately 4–8 $\mu$A/cm$^2$, with the magnitude of the current in individual cases being dependent upon the surface area of the wound. Treatment times ranged from 7 to 72 days, with an average of 30 days; follow-up times ranged from 2 to 22 months with an average of 10 months.

All patients regained their preinjury activity level; all patients with occupational injuries returned to their original or equivalent occupations. Despite the lack of sterile precautions, there were no infections (in one case, a pre-existing post-operative infection was well treated with the silver ions alone).

In all cases, full thickness skin loss was replaced with normal-appearing, full thickness, flexible skin appropriate to the area, with regrowth of subdermal tissues and minimal or no scarification. Initially, the skin appeared to be full-thickness, flexible and innervated; however, it was darker than normal and underwent a subsequent maturation period of several months before gradually acquiring a more normal coloration, dermatoglyphic pattern, and hair growth (in appropriate regions). The normal dermatoglyphic pattern on volar skin areas became more evident with the passage of additional time following treatment. Skin areas were sensitive to light touch, and almost all patients reported the sensation in the area to be subjectively normal without paresthesias, numbness or cold intolerance; only three patients had less than fully normal sensation. Typical results were as follows:

Patient 1. An 11-year-old female lacerated the radial aspect of the left thumb, incurring a full-thickness skin loss of approximately 2 cm$^2$ in area extending from the midpoint of the nail to the mid IP joint and centered over the neutral line between dorsal and volar skin. Treatment using an appropriate voltage was instituted on the day of injury and continued for 28 days.

At the conclusion of treatment, the wound was completely healed with apparently full-thickness skin of a darker than normal coloration, and with good sensation. Normal dorsal-type skin was regenerated dorsal to the neutral line; normal volar skin was formed volar to the neutral line. Coloration and sensation returned to normal over the next month, accompanied by a full range of motion at the IP joint. Thirteen months post-injury, there was no scarring or contracture; sensation was completely normal and the area of the original injury could not be discerned.

Patient 2. A 28-year-old male incurred multiple longitudinal lacerations of the distal phalanx, middle finger right hand, in an industrial accident. On admission, the finger tip was noted to be "filleted" with three deep longitudinal lacerations extending from the dorsal to the palmar surface and proximally into the nail bed with total avulsion of the nail and exposure of the terminal phalanx. The skin over the central portion was insensate.

The wound was immediately irrigated, the various parts loosely approximated with an absorbable suture and dressed with silver-containing nylon fabric, and treated with an appropriate voltage. Antibiotics were given for 3 days starting immediately post-operative. Seven days after start of treatment, there was evident healing of the laceration; treatment was terminated 20 days later. At that time, the skin was almost completely healed, there was a normal contour to the finger tip and sensation was present in the central portion of the wound. Two months after injury, there was minimal scarring on the distal pad, a normal appearing nail was approximately 50% regrown, and normal sensation and range of motion were present. At 12 months follow-up, the finger was asymptomatic, normal in appearance, and fully innervated with normal sensation.

Patient 3. A 33-year-old male utility worker contacted a 7,200-volt electrical line through both hands. He was unconscious for several minutes and incurred burns of the right hypothenar eminence and dorsum of the left hand at the MCP joint line. The hypothenar burn extended from just distal to the 5th MP joint to the base of the 5th metacarpal and consisted of three confluent, ovoid areas of full-thickness skin loss, with a total area of approximately 12 cm$^2$. These areas were blanched and without sensation. The extent of subcutaneous necrosis could not be estimated. The dorsal burn of the left hand involved the second through the fifth MCP joint dorsal surface with full-thickness skin loss over the protuberant areas totaling approximately 4 cm$^2$.

Treatment was begun to both hands on the 4th day after injury, and continued for 16 days on the left hand and 32 days on the right hand. At the end of the treatment, the wounds on the dorsum of the left hand were epithelialized with full-thickenss, flexible skin with good sensation and normal range of motion in the MCP joints. The distal half of the hypothenar wound on the right hand was re-epithelialized with full-thickness sensate skin. The proximate half of the wound was normal in contour and covered with full-thickness skin except for an approximately 1 cm$^2$ area in the center which was covered with thinner skin. Six months after injury, the hypothenar burned area of the right hand was fully innervated and flexible with a normal range of motion of the MCP of the little finger. At that time, the skin was beginning to acquire a normal color and dermatoglyphic pattern.

Figure 7A:
FIG. 7a is a photographic view showing a wound on the foot of a 54-year-old male patient.

Patient 4. A 54-year-old male injured his left foot in a lawnmower accident, resulting in extensive soft tissue injury and open fractures of the 3rd, 4th, and 5th metatarsals and cuboid bone. He underwent debridement and stabilization on the day of the accident. Further debridement was done on the 3rd, 4th, 5th and 23rd days after the accident. Due to the amount of soft tissue loss and bone injury (FIG. 7a), the patient was scheduled for a vascularized composite graft to the injured area. He was given a 50% chance of success, and was advised that the foot might have to be amputated if the surgery failed.

Treatment was initiated on the 32nd day after injury; the patient was placed on oral antibiotics for four weeks. Seventeen days after the start of treatment, the wound was debrided, a portion of avascular bone was removed, and two pins that were projecting into the open wound were removed.

Figure 7B:
FIGS. 7c, 7b, and 7d are photographic views showing the wound of FIG. 7a after thirty-one days, five months, and seven months, respectively, of treatment according to a preferred embodiment of the present invention.
Figure 7C:
Figure 7D:

Thirty-one days after the start of treatment, the gross infection had resolved and the wound was closing very well (FIG. 7b). Over the next four months the wound closed to a small opening (FIG. 7c). At that time, it was felt that an underlying osteomyelitis precluded complete closure of the opening. Therefore, the bone was debrided under local anesthesia and treatment continued. The wound was completely closed and healed within two months thereafter (FIG. 7d). The patient has continued to do well; he has regained an excellent range of motion of the foot with a normal gait pattern.

Figure 8A:
FIG. 8a is a photographic view showing the middle finger of a 21-year-old male patient, after traumatic amputation of one half the distal phalanx at the level of the base of the nail.
Figure 8B:
FIGS. 8b and 8c are photographic views showing the finger of FIG. 8a after 17 days and 38 days, respectively, of treatment according to a preferred embodiment of the present invention.
Figure 8C:
Figure 8D:
FIG. 8d is a photographic view of the finger of FIG. 8a approximately 7 weeks after cessation of treatment.

Patient 5. A 21-year-old male caught the middle finger of his right hand in a metal press, and lost the distal one-half of the distal phalanx of the middle finger at the level of the base of the nail. Treatment according to the present invention was initiated immediately upon presentation, without wound debridement. After 2 days, the patient was pain free and able to change the dressings by himself. Seventeen days after treatment was initiated, regeneration of bone and soft tissue was apparent (FIG. 8b). Thirty-eight days afterwards, the distal phalanx was fully restored with organized, multi-tissue structure; regeneration of appropriate tissues (skin, muscle, nail, etc.) was underway. Treatment was discontinued at this time.

Figure 8E:
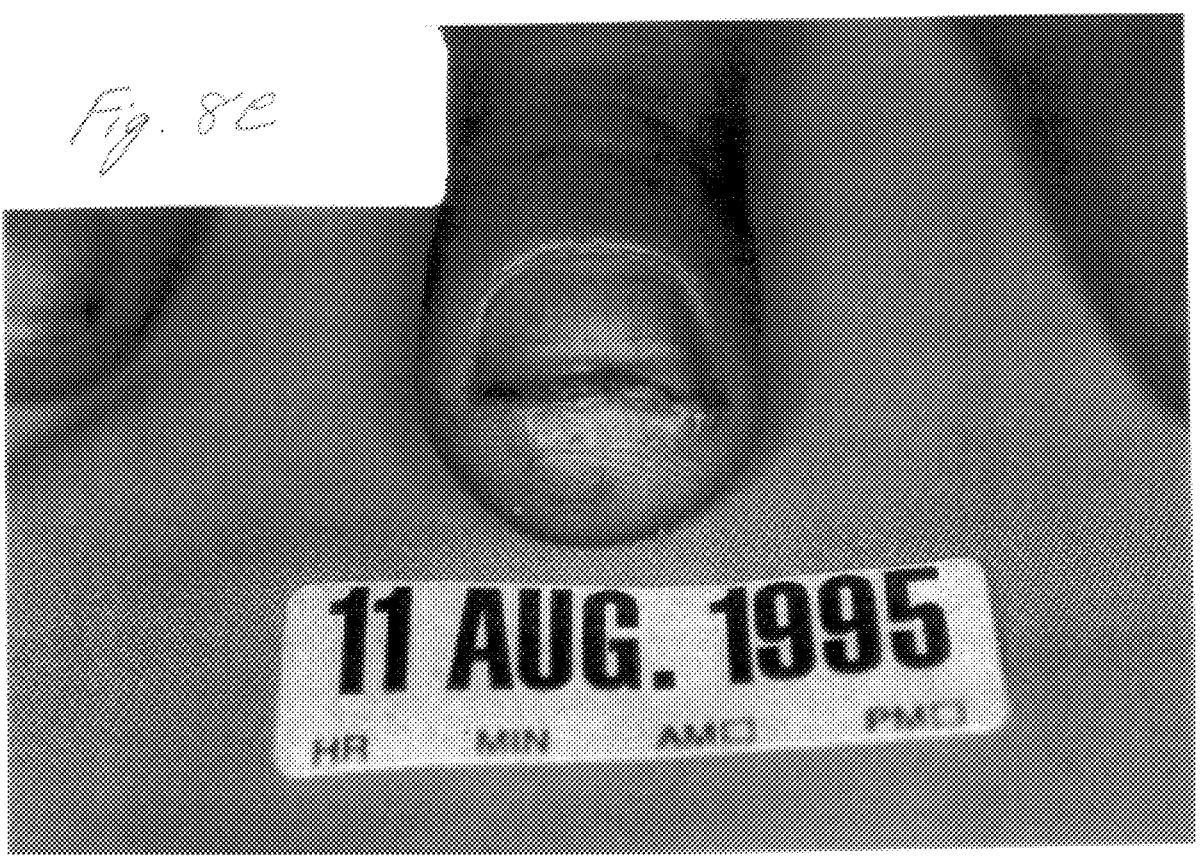
FIG. 8e is a photographic view of the finger of FIG. 8a approximately 7 weeks after cessation of treatment.

Seven weeks after cessation of treatment, the nail was almost completely restored and the volar surface of the finger tip had a normal dermatoglyphic pattern (FIG. 8e). The patient had a full range of motion of the finger and normal sensation of the finger tip, with no permanent physical impairment.

Scaling the treatment voltage to the size of the wound, in conjunction with the other above-identified factors, allows the entry of sufficient numbers of free silver ions into the wound to optimize healing and, in appropriate cases, induce regeneration of missing tissues. It is believed that the observed results were largely due to the action of the silver-collagen complex which produced a large volume of de-differentiated cells in the treatment region. The residual silver-collagen composition in the area is believed to be responsible for the observed long-term continuation of the healing and maturational process after cessation of active treatment, eventually resulting in the restoration of substantially normal function.

It will be apparent to those skilled in the art that many changes and substitutions can be made to the preferred embodiment herein described without departing from the spirit and scope of the present invention as defined by the appended claims.

What is claimed is:

1. A method for treating a wound in a mammalian organism, said wound having a surface area, said method comprising the steps of:

placing a metal-containing anode in contact with said wound;

placing a cathode on intact skin near said anode; and applying an approximately constant DC voltage of approximately 0.09–0.11 V/in$^2$ of said surface area across said anode and said cathode for a sufficient period of time to cause a sufficient number of metal ions from said anode to migrate into a region surrounding said wound so that at least a portion of said metal ions bind to collagen fibers in said region to form a metal-collagen complex.

2. The method as recited in claim 1, wherein said applying step further comprises maintaining said DC voltage for at least approximately 24 hours.

3. The method as recited in claim 1, wherein said applying step further comprises applying approximately 0.1 V/in² of said surface area.

4. The method as recited in claim 1, wherein said anode has a specific resistance no greater than approximately 5 Ω/cm.

5. The method as recited in claim 1, wherein said anode has a specific resistance no greater than approximately 1 Ω/cm.

6. The method as recited in claim 1, wherein said metal is silver.

7. The method as recited in claim 1, wherein said cathode has a specific resistance no greater than approximately 500 Ω/cm.

8. The method as recited in claim 1, further comprising the step of positioning said cathode so that current flow into said wound is approximately uniform.

9. The method as recited in claim 1, further comprising the step of positioning said cathode to maximize current flow through said wound.

10. The method as recited in claim 1, wherein said applying step further comprises causing a sufficient number of said metal ions to migrate from said anode into said region so that another portion of said metal ions causes at least some cells in said region to de-differentiate to form embryonic cells, said metal-collagen complex inducing multiplication of said embryonic cells, said embryonic cells re-differentiating into normal cells as said wound heals.

11. The method as recited in claim 1, wherein said applying step further comprises causing a sufficient number of said metal ions to migrate from said anode into said region so that another portion of said metal combines with chemical species present in said wound to thereby act against bacteria and fungi present therein.

12. A composition for use in inducing healing and regeneration of mammalian tissues, said composition made by a process comprising the steps of:

providing a culture medium containing collagen;

placing a metal-containing anode in contact with a portion of said culture medium, said portion having a surface area;

placing a cathode in contact with another portion of said culture medium; and applying a DC voltage of approximately 0.09–0.11 V/in² of said surface area across said anode and said cathode to cause a sufficient quantity of metal ions from said anode to migrate into said culture medium for a sufficient period of time to cause at least a portion of said collagen to bind to a portion of said metal ions to form a metal-collagen complex.

13. The composition as recited in claim 12, wherein said applying step further comprises applying approximately 0.1 V/in² of said surface area.

14. The composition as recited in claim 12, wherein said metal is silver.

15. The composition as recited in claim 12, wherein said culture medium is a region surrounding a wound, wherein said anode is placed in contact with said wound, and wherein said cathode is placed on intact skin near said anode.

16. A process for making a composition for enhancing wound healing, said process comprising the steps of:

providing a culture medium containing collagen;

placing a metal-containing anode in contact with a portion of said culture medium, said portion having a surface area;

placing a cathode in contact with another portion of said culture medium, said cathode being spaced apart from said anode; and applying a DC voltage of approximately 0.09–0.11 V/in² of said surface area across said anode and said cathode for a sufficient period of time to cause a sufficient quantity of metal ions from said anode to migrate into said culture medium so that at least a portion of said metal ions bind to at least a portion of said collagen to form a metal-collagen complex.

17. The process as recited in claim 16, wherein said anode contains silver.

18. The process as recited in claim 16, wherein said culture medium is a region surrounding a wound, wherein said anode is placed in contact with said wound, and wherein said cathode is placed on intact skin near said anode.

19. The process as recited in claim 16, wherein said applying step further comprises applying said DC voltage for at least approximately 24 hours.

20. A device for inducing tissue healing and regeneration, said device comprising:

a flexible, metal-containing anode;

a cathode;

power supply means capable of generating an approximately constant DC voltage across said anode and said cathode when said anode is placed in contact with a wound having a surface area and said cathode is placed on substantially intact skin near said wound; and means for electrically connecting said power supply means to said anode and said cathode, said anode containing a sufficient quantity of said metal to maintain a DC voltage of approximately 0.094–0.11 V/in² of said wound surface area.

21. The device as recited in claim 20, wherein said anode has a specific resistance no greater than approximately 1 Ω/cm.

22. The device as recited in claim 20, wherein said cathode has a specific resistance no greater than approximately 500 Ω/cm.

23. The device as recited in claim 20, wherein said metal is silver.

24. The device as recited in claim 20, wherein said anode contains a sufficient quantity of said metal to maintain said approximately constant DC voltage for at least approximately 24 hours.

25. The device as recited in claim 20, wherein said power source has a plurality of output terminals, each of said output terminals having a different output voltage, and wherein said anode further comprises a plurality of anodes, each of said anodes corresponding to one of said output terminals.

26. The device as recited in claim 20, wherein said anode has a specific resistance no greater than approximately 5 W/cm.

27. A method for treating a wound, said method comprising the steps of:

placing a metal-containing anode in contact with said wound, said anode having a specific resistance no greater than approximately 5 W/cm;

placing a cathode on intact skin near said anode; and applying an approximately constant DC voltage across said anode and said cathode for a sufficient period of time to cause a sufficient number of metal ions from said anode to migrate into a region surrounding said wound so that at least a portion of said metal ions bind to collagen fibers in said region to form a metal-collagen complex.

28. The method as recited in claim 27, wherein said applying step further comprises maintaining said DC voltage for at least approximately 24 hours.

29. The method as recited in claim 27, wherein said wound has a surface area, and wherein said applying step further comprises applying approximately 0.09–0.11 V/in$^2$ of said surface area.

30. The method as recited in claim 27, wherein said metal is silver.

31. The method as recited in claim 27, wherein said cathode has a specific resistance no greater than approximately 500 W/cm.

32. The method as recited in claim 27, further comprising the step of positioning said cathode to optimize current flow through said wound.

33. A device for inducing tissue healing and regeneration, said device comprising:
 a flexible, silver-containing anode, said anode having a specific resistance no greater than approximately 5 W/cm;
 a cathode;
 power supply means capable of generating an approximately constant DC voltage across said anode and said cathode when said anode is placed in contact with a wound and said cathode is placed on substantially intact skin near said wound; and
 means for electrically connecting said power supply means to said anode and said cathode.

34. The device as recited in claim 33, wherein said cathode has a specific resistance no greater than approximately 500 W/cm.

35. The device as recited in claim 33, wherein said anode contains a sufficient quantity of said silver to maintain said approximately constant DC voltage for at least approximately 24 hours.

36. The device as recited in claim 33, wherein said wound has a surface area, and wherein said anode contains a sufficient quantity of said silver to maintain a DC voltage of approximately 0.09–0.11 V/in$^2$ of said surface area.

37. The device as recited in claim 33, wherein said power source has a plurality of output terminals, each of said output terminals having a different output voltage, and wherein said anode further comprises a plurality of anodes, each of said anodes corresponding to a different one of said output terminals.

38. A process for making a composition for enhancing wound healing, said process comprising the steps of:
 providing a culture medium containing collagen;
 placing a silver-containing anode in contact with a portion of said culture medium, said portion having a surface area;
 placing a cathode in contact with another portion of said culture medium, said cathode being spaced apart from said anode;
 applying a sufficient DC voltage across said anode and said cathode for a first period of time, thereby causing silver ions from said anode to migrate into said culture medium and combine with chemical species present therein;
 continuing to apply said DC voltage for a second period of time, thereby causing additional silver ions from said anode to associate with silver-sensitive cells in said culture medium to cause de-differentiation of said cells into embryonic cells; and
 continuing to apply said DC voltage for a third period of time, thereby causing additional silver ions from said anode to bind to at least a portion of said collagen to form a silver-collagen complex, said silver-collagen complex inducing multiplication of said de-differentiated cells, said embryonic cells re-differentiating into normal cells as said wound heals.

39. The process as recited in claim 28, wherein said applying step further comprises maintaining said DC voltage for at least approximately 24 hours.

40. The method as recited in claim 38, wherein said wound has a surface area, and wherein said applying step further comprises applying approximately 0.09–0.11 V/in$^2$ of said surface area.

41. The method as recited in claim 38, wherein said anode has a specific resistance no greater than approximately 5 W/cm.

42. The method as recited in claim 38, wherein said cathode has a specific resistance no greater than approximately 500 W/cm.

* * * * *